United States Patent
Nakamura et al.

(10) Patent No.: US 7,141,389 B1
(45) Date of Patent: *Nov. 28, 2006

(54) CHROMOSOME DNA CODING FOR HUMAN HEPATOCYTE GROWTH FACTOR

(76) Inventors: Toshikazu Nakamura, 11-6, Midorigaoka 3-chome, Higashi-ku, Fukuoka-shi, Fukuoka (JP); Tatsuya Seki, c/o Toyo Boseki Kabushiki Kaisha, Pharmaceuticals Research Center, 1-1, Katata 2-chome, Ohtsu-shi, Shiga 520-02 (JP); Michio Hagiya, c/o Toyo Boseki Kabushiki Kaisha, Pharmaceuticals Research Center, 1-1, Katata 2-chome, Ohtsu-shi, Shiga 520-02 (JP); Manabu Shimonishi, c/o Toyo Boseki Kabushiki Kaisha, Pharmaceuticals Research Center, 1-1, Katata 2-chome, Ohtsu-shi, Shiga 520-02 (JP); Shin Shimizu, c/o Toyo Boseki Kabushiki Kaisha, Pharmaceuticals Research Center, 1-1, Katata 2-chome, Ohtsu-shi, Shiga 520-02 (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/292,160

(22) Filed: Aug. 17, 1994

Related U.S. Application Data

(63) Continuation of application No. 07/705,741, filed on May 28, 1991.

(30) Foreign Application Priority Data

Nov. 19, 1990 (JP) ................................. 2-314548

(51) Int. Cl.
*C12N 1/16* (2006.01)
*C12N 5/16* (2006.01)
*C12N 15/18* (2006.01)
*C12N 15/63* (2006.01)
*C12N 1/21* (2006.01)

(52) U.S. Cl. ..................... 435/69.4; 435/325; 435/365; 435/254.2; 435/243; 435/320.1; 536/23.51

(58) Field of Classification Search ............... 435/69.1, 435/69.4, 240.1, 240.2, 252.1, 252.3, 252.33, 435/320.1, 243, 325; 536/23.5, 23.1
See application file for complete search history.

(56) References Cited

U.S. PATENT DOCUMENTS 5,004,805 A * 4/1991 Gohda et al. ............... 530/399

OTHER PUBLICATIONS

Seki et al, "Isolation and Expression of CDNA for Different Forms of Hepatocyte Growth Factor . . . " BBRC, 172 (1) p. 321-327, Oct. 15, 1990.*
Winnocker, E. in *From Genes to Clones* p. 384-389, 1987.*
Ayala et al. Modern Genetics. Benjamin/Cummings Publishing Co. 1984, p. 694.*
Miyazawa et al. Biochm. biophys. Res. Commun. 163(2): 967-973, Sep. 1989.*

* cited by examiner

*Primary Examiner*—Christine J. Saoud
(74) *Attorney, Agent, or Firm*—Leydig, Voit & Mayer, Ltd

(57) ABSTRACT

A chromosome DNA which codes for human hepatocyte growth factor, a recombinant expression vector capable of expressing the DNA, a transformant transformed with the expression vector and a method of producing recombinant human hepatocyte growth factor. The DNA and polypeptide of the present invention are expected to serve well for hepatocyte cultivation reagents, liver regeneration promoters, various researches, clinical diagnostic reagents and therapeutic drugs for liver diseases.

8 Claims, 3 Drawing Sheets

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 728 amino acids
      (B) TYPE: amino acid
      (D) TOPOLOGY: linear (ii) MOLECULE TYPE: peptide (xi) SEQUENCE DESCRIPTION: SEQ ID NO:1:

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190
```

-continued

```
Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
```

```
        610                 615                 620
Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
                675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

(2) INFORMATION FOR SEQ ID NO:2:

(i) SEQUENCE CHARACTERISTICS:
        (A) LENGTH: 723 amino acids
        (B) TYPE: amino acid
        (D) TOPOLOGY: linear (ii) MOLECULE TYPE: peptide (xi) SEQUENCE DESCRIPTION: SEQ ID NO:2:

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
                35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
                115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
                180                 185                 190

Tyr Glu Val Cys Asp Ile Pro Gln Cys Ser Glu Val Glu Cys Met Thr
                195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240
```

-continued

```
Leu Pro Glu Arg Tyr Pro Asp Lys Gly Phe Asp Asp Asn Tyr Cys Arg
            245                 250                 255
Asn Pro Asp Gly Gln Pro Arg Pro Trp Cys Tyr Thr Lys Asp Pro His
            260                 265                 270
Thr Arg Trp Glu Tyr Cys Ala Ile Lys Thr Cys Ala Asp Asn Thr Met
            275                 280                 285
Asn Asp Thr Asp Val Pro Leu Glu Thr Thr Glu Cys Ile Gln Gly Gln
            290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
            325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
            355                 360                 365
Val Gly Tyr Cys Ser Gln Ile Pro Asn Cys Asp Met Ser His Gly Gln
            370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
            405                 410                 415
Leu His Arg His Ile Phe Trp Glu Pro Asp Ala Ser Lys Leu Asn Glu
            420                 425                 430
Asn Tyr Cys Arg Asn Pro Asp Asp Ala His Gly Pro Trp Cys Tyr
            435                 440                 445
Thr Gly Asn Pro Leu Ile Pro Trp Asp Tyr Cys Pro Ile Ser Arg Cys
            450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
            485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
            515                 520                 525
Gln Cys Phe Pro Ser Arg Asp Leu Lys Asp Tyr Glu Ala Trp Leu Gly
            530                 535                 540
Ile His Asp Val His Gly Arg Gly Asp Glu Lys Cys Lys Gln Val Leu
545                 550                 555                 560
Asn Val Ser Gln Leu Val Tyr Gly Pro Glu Gly Ser Asp Leu Val Leu
            565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
            595                 600                 605
Val Tyr Gly Trp Gly Tyr Thr Gly Leu Ile Asn Tyr Asp Gly Leu Leu
            610                 615                 620
Arg Val Ala His Leu Tyr Ile Met Gly Asn Glu Lys Cys Ser Gln His
625                 630                 635                 640
His Arg Gly Lys Val Thr Leu Asn Glu Ser Glu Ile Cys Ala Gly Ala
            645                 650                 655
```

-continued

```
Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser
```

(2) INFORMATION FOR SEQ ID NO:3:

(i) SEQUENCE CHARACTERISTICS:
        (A) LENGTH: 1268 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 1...29)
        (B) LOCATION: 1081..1168

(xi) SEQUENCE DESCRIPTION: SEQ ID NO:3:

```
AAAGTCAGTC CTAACCAGTG TATACGTACA TACACACCAA CATGTGTGAA TGTGTTGTGT        60

GCACGTGTGT CCTGTACAAG TCCACATGGC ATATTTACCT GTCAGGGACA GGCTATGGAC       120

AATGACTGTT TCTTGGACTT TCTCTTAAAA AGTCAGATCA GACAAGTTTC TTTTGTATAC       180

TTTGGGTAAA TGTGTGGTAT TTCGTGAGTT TGGAGTTTGT GAAAAAAAAA AAAAAAAAAA       240

AAAAAAAAAA AGCTGCCTGC TCTGAGCCCA TGGGGCAGGG GCAATTTTTT CATCTGACAA       300

TCTGCGTGCT TTTGTTTTGC TTGCTTATTT TGGCCCCACA ATACCACACC CTTTTCTTAA       360

CTAACCTCTT TCTACCTGGG CTGGACGTGC CTGGGCTCTC CTCCCTGGCC CCGCTCCCAC       420

CTCTCCCAGG TCTCTAAACC CCTAGAGAAC CTGTGTCAGT GTTTTGAATC CCTCAGTTGC       480

TCTAGCAGGA AAACTAGACA GATTAGGAGC TGGGCACAT TTGGCTGAAA GACAGCTCTT        540

CGCTTTCTTC TTATGCTGCT TCCCCTTCCT CTTTTCCCAA ATAGATATAT AAACACATGT       600

ATTTTCCTGT TTAAATTGAG CGAATTGGTC CCCTGCCTGT GCCTTGATTT AGCCATTGGG       660

CTCAGCCTTG CTCCTCCCTT CCTTACTCGG ATAGGAGCCA CTGGGATCTG GAGCTCCAGC       720

TTCCAAATTG AAGCTGGCCT CAGGCCAGGT GACTTTTCTT TGTAAGTTTC TTTCCTAAGC       780

GTGGGGTTGG GGGGAGGCGG GGAATGGGGG GGGTTGCAGG GATCTGTTTG GTGCTGTTGA       840

AGGGGGGGCG AGTGAGGAAA GGAGGGGGCT GGAAGAGAGT AAAGGGCTGT TGTTAAACAG       900

TTTCTTACCG TAAGAGGGAG TTCAGACCTA GATCTTTCCA GTTAATCACA CAACAAACTT       960

AGCTCATCGC AATAAAAAGC AGCTCAGAGC CGACTGGCTC TTTTAGGCAC TGACTCCGAA      1020

CAGGATTCTT TCACCCAGGC ATCTCCTCCA GAGGGATCCG CCAGCCCGTC CAGCAGCACC      1080

ATGTGGGTGA CCAAACTCCT GCCAGCCCTG CTGCTGCAGC ATGTCCTCCT GCATCTCCTC      1140

CTGCTCCCCA TCGCCATCCC CTATGCAGGT TAGTTCCCTT CTTCTTCTTC ATTATTAGTA      1200

TTAGTATTTA ACTCTCCTGC TAACCTTCCC TATTCCTTTT AACACCCTCT TTTTACCCTA      1260

TTCCCAGC                                                              1268
```

(2) INFORMATION FOR SEQ ID NO:4:

(i) SEQUENCE CHARACTERISTICS:

(A) LENGTH: 366 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 30...85)
        (B) LOCATION: 101..266

(xi) SEQUENCE DESCRIPTION: SEQ ID NO:4:

```
AATCACTTTC TTGTAGATGA TCCTTAGGAT TTTTTTTATA TATGAGCCTT AAAAACATTT      60

CTCCAATGTT TATTTTTTTA AAACATTTTG TATTTAATAG AGGGACAAAG GAAAAGAAGA     120

AATACAATTC ATGAATTCAA AAAATCAGCA AAGACTACCC TAATCAAAAT AGATCCAGCA     180

CTGAAGATAA AAACCAAAAA AGTGAATACT GCAGACCAAT GTGCTAATAG ATGTACTAGG     240

AATAAAGGAC TTCCATTCAC TTGCAAGTAA GTTACTTCAT TTTCTTCTTA GAATAATTTT     300

CCAAATATAG CATGCATGTA TTATAATCAT GTGTCTTTTG TGTTGTAGTC AATGTGATTT     360

GATCAT                                                                366
```

(2) INFORMATION FOR SEQ ID NO:5:

(i) SEQUENCE CHARACTERISTICS:
        (A) LENGTH: 313 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 86...122)
        (B) LOCATION: 101..213

(xi) SEQUENCE DESCRIPTION: SEQ ID NO:5:

```
ATATTGTCCA TATGCCCATG GACAAGATGA ACCATATGCG CATTCTTTAA ATACTGTATA      60

ATAGTAGTAT TTCTTCTTTT CATTCTGATA TTTTTTTCAG GGCTTTTGTT TTTGATAAAG     120

CAAGAAAACA ATGCCTCTGG TTCCCCTTCA ATAGCATGTC AAGTGGAGTA AAAAAAGAAT     180

TTGGCCATGA ATTTGACCTC TATGAAAACA AAGGTAACTG ACTTCTCCCT AAATATTGCA     240

TAATGAAATA AAGTATAATG AAATGTATGT TTGTAATTTC CTGCCAGAGT GGTCTTTCTC     300

ACTGATTTTT CTA                                                        313
```

(2) INFORMATION FOR SEQ ID NO:6:

(i) SEQUENCE CHARACTERISTICS:
        (A) LENGTH: 315 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 123...161)
        (B) LOCATION: 101..215

(xi) SEQUENCE DESCRIPTION: SEQ ID NO:6:

```
TTACAAGAGT TAATTACTTA CAGGTTTGAA CGGAATTTTT TTCTTAAATA CTGCATATGT      60

TTTGCATAGT TGCAATAATT TTATCTACTT TCTTCAATAG ACTACATTAG AAACTGCATC     120

ATTGGTAAAG GACGCAGCTA CAAGGGAACA GTATCTATCA CTAAGAGTGG CATCAAATGT     180
```

```
CAGCCCTGGA GTTCCATGAT ACCACACGAA CACAGGTAAG AACAGTATGA AGAAAAGAGA      240

TGAAGCCTCT GTCTTTTTTA CATGTTAACA GTCTCATATT AGTCCTTCAG AATAATTCTA      300

CAATCCTAAA ATAAC                                                       315
```

(2) INFORMATION FOR SEQ ID NO:7:

(i) SEQUENCE CHARACTERISTICS:
        (A) LENGTH: 343 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 162...208 in SEQ ID NO:1;
            amino acids 162...203 in SEQ ID NO:2)
        (B) LOCATION: 101..243 for SEQ ID NO:1; 116...243 for
            SEQ ID NO:2

(xi) SEQUENCE DESCRIPTION: SEQ ID NO:7:

```
TTTCTACCTT CAGCAAAAAC ATACCCACTA ATTAGTAAAA TTAATAGGCA AAAAAAGTT        60

GCATGCTCTT ATACTGTAAT GATTATCATT TTAAAACTAG CTTTTTGCCT TCGAGCTATC      120

GGGGTAAAGA CCTACAGGAA AACTACTGTC GAAATCCTCG AGGGGAAGAA GGGGGACCCT      180

GGTGTTTCAC AAGCAATCCA GAGGTACGCT ACGAAGTCTG TGACATTCCT CAGTGTTCAG      240

AAGGTAAATA AACCTGAATG CCATGTGGGC CATTCTATTC CCCCTATGTG TAGAACTGTA      300

ACTCACATTA AAGGTTAACA GCAACGAATC AATCATAACA AAT                        343
```

(2) INFORMATION FOR SEQ ID NO:8:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 209...249 in SEQ ID NO:1;
            amino acids 204...244 in SEQ ID NO:2)
        (B) LOCATION: 101..221

(xi) SEQUENCE DESCRIPTION: SEQ ID NO:8:

```
AAATCTGTTT ACTAAACAGG TGCTGTTCTT TAAATGGAAC AGTGGTGTTT TTGATTTTGC       60

TGTCAGAAAC AATTAACATG CCATACTTTA ATTTTATTAG TTGAATGCAT GACCTGCAAT      120

GGGGAGAGTT ATCGAGGTCT CATGGATCAT ACAGAATCAG GCAAGATTTG TCAGCGCTGG      180

GATCATCAGA CACCACACCG GCACAAATTC TTGCCTGAAA GGTAAAATAT TAATGAATCA      240

TGCTTTCAGT GATTCTTTAC AAACTATTAT TCACTCTATG ACACACTGCT GTGGAAATTC      300

TCTTTATATT ATGTTTTCCC G                                                321
```

(2) INFORMATION FOR SEQ ID NO:9:

(i) SEQUENCE CHARACTERISTICS:
        (A) LENGTH: 319 base pairs
        (B) TYPE: nucleic acid
        (C) STRANDEDNESS: double
        (D) TOPOLOGY: linear (ii) MOLECULE TYPE: DNA (genomic)

(ix) FEATURE:

(A) NAME/KEY: exon (amino acids 250...288 in SEQ ID NO:1;
            amino acids 245...283 in SEQ ID NO:2)
        (B) LOCATION: 101..219

(xi) SEQUENCE DESCRIPTION: SEQ ID NO:9:

TAGGTGTAGA CAACCTAAGT GGAAAGTTAT TTTGTGAGCT GAGGGGTGGG TGGTGTTTCC    60

AGGCAGATTT ACGTGACACT TTTCTTGGTG TGGTTTGCAG ATATCCCGAC AAGGGCTTTG   120

ATGATAATTA TTGCCGCAAT CCCGATGGCC AGCCGAGGCC ATGGTGCTAT ACTCTTGACC   180

CTCACACCCG CTGGGAGTAC TGTGCAATTA AACATGCGG TAAGTGAAGG TCAAATTTAT    240

TGCTTCCTTT TCCTCTCACA GACTGGATCT AAGCAGGCGA TTATTAGTGA GACAGGTAA    300

CAACTATTTA ACTTGATGC                                                319

(2) INFORMATION FOR SEQ ID NO:10:

(i) SEQUENCE CHARACTERISTICS:
        (A) LENGTH: 375 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 289...347 in SEQ ID NO:1;
            amino acids 284...342 in SEQ ID NO:2)
        (B) LOCATION: 101..275

(xi) SEQUENCE DESCRIPTION: SEQ ID NO:10:

AAAAAAATCT GCTAATACAA ATGCCAATGA ACTCTAAGAG GCAAATGACA TCTTCAAAGA    60

TTTTATATAA GTTTTTTTTG TTGTTGTTTT TTGCCAATAG CTGACAATAC TATGAATGAC   120

ACTGATGTTC CTTTGGAAAC AACTGAATGC ATCCAAGGTC AAGGAGAAGG CTACAGGGGC   180

ACTGTCAATA CCATTTGGAA TGGAATTCCA TGTCAGCGTT GGGATTCTCA GTATCCTCAC   240

GAGCATGACA TGACTCCTGA AAATTTCAAG TGCAAGTGAG TAAAGTAGGC AAATGTTATA   300

CATTTCAGTA GGCCCTGGGG AAAATGAGGT AGAGTGGTTA CTTTTTACTA ATTTTGTGTT   360

AGTGATCAAA CTTCA                                                    375

(2) INFORMATION FOR SEQ ID NO:11:

(i) SEQUENCE CHARACTERISTICS:
        (A) LENGTH: 328 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 348...389 in SEQ ID NO:1;
            amino acids 343...384 in SEQ ID NO:2)
        (B) LOCATION: 101..228

(xi) SEQUENCE DESCRIPTION: SEQ ID NO:11:

ATAAACATGC ATACATTCTA GAATTCTAGA AATGTAAATAG CGCTGACTTC ACCAACGTAA   60

GAACTCCGGC AATTTACATT AACATGCTTA TTCTCAATAG GACCTACGA GAAAATTACT   120

GCCGAAATCC AGATGGGTCT GAATCACCCT GGTGTTTTAC CACTGATCCA AACATCCGAG   180

TTGGCTACTG CTCCCAAATT CCAAACTGTG ATATGTCACA TGGACAAGGT AATAGCTGAC   240

ATTCTGCAGG GTGGGCATGA TTAAATTCAG GGGAAATGCC TAAAGGGAGG ACACATTTTA   300

CAGCATAAGA TCTACTTCTT GCTGCACT                                      328

(2) INFORMATION FOR SEQ ID NO:12:

(i) SEQUENCE CHARACTERISTICS:
        (A) LENGTH: 303 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 390...424 in SEQ ID NO:1;
            amino acids 385...419 in SEQ ID NO:2)
        (B) LOCATION: 101..203

(xi) SEQUENCE DESCRIPTION: SEQ ID NO:12:

| | | | | | |
|---|---|---|---|---|---|
| TTTTTATGTT | GATTTCATGA | TTCCATATAC | TTGTAAAAAA | TCTTTTTGTT | TTATCCGCCT | 60 |
| TGATATTCAT | TGGACTTATT | TCTGTATATT | TTATGTCTAG | ATTGTTATCG | TGGGAATGGC | 120 |
| AAAAATTATA | TGGGCAACTT | ATCCCAAACA | AGATCTGGAC | TAACATGTTC | AATGTGGGAC | 180 |
| AAGAACATGG | AAGACTTACA | TCGGTGTGTA | AATTTCTTCC | TTTCAATATA | TAGAATGTAG | 240 |
| TGATACCAAC | AGACTGTGTA | TTTAGATATG | TACATTGCTA | TTTCTTTCTA | TTCTTTTATA | 300 |
| TAT | | | | | | 303 |

(2) INFORMATION FOR SEQ ID NO:13:

(i) SEQUENCE CHARACTERISTICS:
        (A) LENGTH: 334 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 425...468 in SEQ ID NO:1;
            amino acids 420...463 in SEQ ID NO:2)
        (B) LOCATION: 101..234

(xi) SEQUENCE DESCRIPTION: SEQ ID NO:13:

| | | | | | |
|---|---|---|---|---|---|
| CAGTGAAAGT | AATGTGCTGA | GATTATATCT | TTTTGTAATA | TTTTGTGTCT | CTTGGATGGA | 60 |
| ATGAGCATCT | TGTGATGTGC | AAGGCCTGTT | GTTTCCGCAG | TCATATCTTC | TGGGAACCAG | 120 |
| ATGCAAGTAA | GCTGAATGAG | AATTACTGCC | GAAATCCAGA | TGATGATGCT | CATGGACCCT | 180 |
| GGTGCTACAC | GGGAAATCCA | CTCATTCCTT | GGGATTATTG | CCCTATTTCT | CGTTGTAAGT | 240 |
| ACAGTTAGGG | ATTGGTGTCT | TGTGAAATAT | TTTAAATGTA | CTACATTTCA | TCTAAAAGTT | 300 |
| GTAAATAATA | TAGGTGGTCT | GGCATTTATT | CCCA | | | 334 |

(2) INFORMATION FOR SEQ ID NO:14:

(i) SEQUENCE CHARACTERISTICS:
        (A) LENGTH: 239 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 469...481 in SEQ ID NO:1;
            amino acids 464...476 in SEQ ID NO:2)
        (B) LOCATION: 101..139

(xi) SEQUENCE DESCRIPTION: SEQ ID NO:14:

```
CTGAATTCAT TGATACTTGG ATTTTAATAT ATATTTGGTT TTATATAACA GATATATGCA      60

TATATGAATT GTGTATTTAT CTATACATTT ATTTTTACAG GTGAAGGTGA TACCACACCT     120

ACAATAGTCA ATTTAGACCG TAAGTAATAT TTCACAATAT AAAGTATATC TGAGTCTCTC     180

TCTGTGTGTC AGAAGTGTCA TTATTTCTTT CAAAGAAAAT TATCTATATT AGCTTCCAT     239

(2) INFORMATION FOR SEQ ID NO:15:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 482...514 in SEQ ID NO:1;
            amino acids 477...509 in SEQ ID NO:2)
        (B) LOCATION: 101..197

(xi) SEQUENCE DESCRIPTION: SEQ ID NO:15:

AGTTACATTT GTGTAATTAT CATTGCATTT AAGAAAACTA AGAGGCACTG ATTATTTCAA      60

ATTCTTATTT TAAAAAATGT TATGTTTGGT CCTGTTTCAG ATCCCGTAAT ATCTTGTGCC     120

AAAACGAAAC AATTGCGAGT TGTAAATGGG ATTCCAACAC GAACAAACAT AGGATGGATG     180

GTTAGTTTGA GATACAGGTA ATTATTAATA GATGCAAGTC ATGCATATCC AGAATATGTA     240

CAAGAGAGTC CTATTCCCAG AAATATGGAC ACATGTGGTC CTGAAGGTTG TACCCTC       297

(2) INFORMATION FOR SEQ ID NO:16:

(i) SEQUENCE CHARACTERISTICS:
        (A) LENGTH: 275 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 515...539 in SEQ ID NO:1;
            amino acids 510...534 in SEQ ID NO:2)
        (B) LOCATION: 101..175

(xi) SEQUENCE DESCRIPTION: SEQ ID NO:16:

GTGTATTTAT TTTTAACAAA TGGAGCCACA GGCTTTGCAT TAATTGGCAG TCACTCTTTC      60

TGCACAGATG TTACTTGTTT CTCTTTCCTC TTTTTCACAG AAATAAACAT ATCTGCGGAG     120

GATCATTGAT AAAGGAGAGT TGGGTTCTTA CTGCACGACA GTGTTCCCT TCTCGGTAAA      180

GTGTTTTTAA AACTAGTATT ATTTTGAGCC TTTAAAATGT GTATGTCTTC CACTTTGCTC     240

TTAAGGTTAT AATATGTATT CATTTTACAG AGATT                               275

(2) INFORMATION FOR SEQ ID NO:17:

(i) SEQUENCE CHARACTERISTICS:
        (A) LENGTH: 7753 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon (amino acids 540...586 in SEQ ID NO:1;
            amino acids 535...581 in SEQ ID NO:2)
        (B) LOCATION: 102..242
```

(ix) FEATURE:
    (A) NAME/KEY: exon (amino acids 587...621 in SEQ ID NO:1;
        amino acids 582...616 in SEQ ID NO:2)
    (B) LOCATION: 774..878

(ix) FEATURE:
    (A) NAME/KEY: exon (amino acids 622...670 in SEQ ID NO:1;
        amino acids 617...665 in SEQ ID NO:2)
    (B) LOCATION: 990..1136

(ix) FEATURE:
    (A) NAME/KEY: exon (amino acids 671...728 in SEQ ID NO:1;
        amino acids 666...723 IN SEQ ID NO:2)
    (B) LOCATION: 3764..3937

(xi) SEQUENCE DESCRIPTION: SEQ ID NO:17:

```
GTTATGTGCC TTAATAGTCT AAAATAACAA TAGATAGGAA TAATACTACA GAATTTGGAA     60
TTATTATGTT TTACATTTAA ATTTTTTTCC TTCAAAACAG AGACTTGAAA GATTATGAAG    120
CTTGGCTTGG AATTCATGAT GTCCACGGAA GAGGAGATGA GAAATGCAAA CAGGTTCTCA    180
ATGTTTCCCA GCTGGTATAT GGCCCTGAAG GATCAGATCT GGTTTTAATG AAGCTTGCCA    240
GGTTAGTTAC TTTAGAAGAT TTTGTATTTT TCACCTGGAC AAGAATTGTT GGAGCATTTT    300
CTTCAGCTGT GTGGCAGTTC GTTCTCTCTC ATACAGATGC ATTATAAACA TATGTTACAT    360
GCTGTATATA TATGTATATA TGCATGCGTT TGGGTCTCTC TGTGAGTATA GAGAGAAAGG    420
TATTTGCAAA ACTGTAAAAA AATGAATAAC TAACATTGGG CCAACAGTCT GATCAGTCTG    480
TTTTAAAATG GAAACTCAGC AGTTATTTGA TAACTTTCAA ATGTAAAATA ATTATTTTAA    540
AAAATAGCAT TGACCATTTA TTCTTAAATA TTGGCAAATA CATGACTCAT TTCTTTACTA    600
CCTATTCCAA ATGTCATCAT TACATTTGGA CATTCCCACC TTTTTTTTTT TTTTTTAAGA    660
AACAGGACTT CATTCTCTGT AAATGCCATA TTAAACATGA ACACTACATT AATATGTTA    720
ATTTTGTGTT GTTACCAGTT GAGAGTACTT ACCATGTATT TTGTGTTTTC AGGCCTGCTG    780
TCCTGGATGA TTTTGTTAGT ACGATTGATT TACCTAATTA TGGATGCACA ATTCCTGAAA    840
AGACCAGTTG CAGTGTTTAT GGCTGGGGCT ACACTGGATG TAAGCTAGTT TTCAAAAGAT    900
GAGGCCATAT TTATTTTATT TTAAAAAGAA CACATTTGTC TTTGTTTCTT ACTTTTCTCA    960
CCTTATTGTA TGTTTTTTGC ATCAATCTAG TGATCAACTA TGATGGCCTA TTACGAGTGG   1020
CACATCTCTA TATAATGGGA AATGAGAAAT GCAGCCAGCA TCATCGAGGG AAGGTGACTC   1080
TGAATGAGTC TGAAATATGT GCTGGGGCTG AAAAGATTGG ATCAGGACCA TGTGAGGTAA   1140
AAAGGAAGTT CTTTAATAAG GAGTATGTGA TTCATAGCTT AGTGTTTCAT GTTTATTTTT   1200
TTCTGTTTAT TTTTCTCAAA TCAAAAATAT TGTATACCAA CCTATTCTAG GAAAGAGGAA   1260
TTGGGAAAAT TAACTCTGTA ATATTCTGCA TTTCTTTCAA CTAAGCAGTG AGATAATCAA   1320
TGTTTTATTA GCAGCAAACT ATGATGACAT TTGTCACTCA AAAAATAATA AGTGTGTAGA   1380
GCCGGAACTC CAAGGGAGAG CTATTCAAAT GAGAAGTATC CAAATCAGTT AGATCAATGG   1440
TTTGCATTTT TCTAATGTTT TTCTAAATTT ATTTTATCTT CCCAAATTAT CTCGAAGTGA   1500
ACTCCACTAA TTATATCATT CAGAGAGGTC CTGGCTTAAA CTTTTAAATC TCTTTTTGGG   1560
TAAGCTGTTC CCTCTTTTGC TCTCTCGCTC TGTGTATGTG TTTAAACAGA TTCTATTTTA   1620
AAAAGCCTAA GGTCAAAGTT TGTGACTTTA CGAGCTTGGA CATTTCATTT GTGAGGCAAC   1680
TGTTATTTCG GCTTGGCAAT GTTCCTATCC CTATTTTACA TAGACAAGCT GTTAAACTGT   1740
TAGTTTAGTT AGATTTTGAA TGTGAGAGAC ATGTTCTCCA AGCTTCAGGG CTGTGGGATT   1800
GTGGAATGCT GTGTGTGGCA AAAGATGAAA TGAGTTCAAT GATAGTGAAA TGTCCTTTGA   1860
```

```
TATGTAGGAA AATGCATGCT GTAAGTATGG AACATAAATA TGTATTGAAA TGCAAGTGTT      1920

ATACACCTTG CTCTGAGATT TTATTTCTGA AAAGAAGAGA AAATGTTTAC TGTTTACTGA      1980

GTTTTTAGAA CTGCTTAAAA ATGATATGGT TAGAAACAGA TTATATGTTT ATAACCAGTT      2040

TCAAATTTGT TGCCTTTCTA GTAAATCATG AACAATGAAA CCATTGTTCA TTATAACAAG      2100

GGAACATTTA CTAGGAGAAA TAAATGACTA TACTTTAAAA AGAAAAAGCA ATAAGCATCC      2160

GGGAAACACA GAAGTTTCTA ACTAGACCCA ACCTTACAGA TCATCTAATT ATTGTCATTA      2220

CCAAAACCAA TTTGACAACT GCTTTTGAAG AATAGCCTTT AATTTGGATT ATCACCTATA      2280

TATTTTTCAC TTCCCTCTTC AGTTTGAATT ATTCATATCT GTATACTATA TATGTTGTTT      2340

TTAACTTTAT TGATAAGACT TGACCTCAAG TAGATTCCGC CACTTCTCAA AAATGTATTT      2400

ATCCTCCAGA ATGTTTTTAA AAATATATAT GTCACTGACA TTTAAATCAA GGTAATTTAG      2460

CCACTGAAAT AAATTTGAAG GAGATATCTC CCAAATGTTT GTATAATAGC AGTAACATCA      2520

TATTTAGTGA AAGTCTCCAG AGTGAATTAC TTTGAGGAGT TTGTCTCAGT AATCACTAGT      2580

ACATTTGTTT AAAAATCAGT TTTCTTTCCT CAACTGGCAT AGTTTATATA GTCTCTTGGA      2640

ATAAACTATT TTTGTTTACT GTTTGAAATT CTACTTTACC CCTAACTTGG TTTTCCCCAT      2700

CACAGAATGC CAATGCTCTC TTCTTTCCAT TTGAATCACA TAAGTTAATT TTGCAGTGGT      2760

TTCCCCCATC GCTGTTTAGG GAAAATTAAG GTAGTTCCAA ACACTCTTCT GCATATAAAG      2820

ATACCAAAAG CCAGCCACTG CATTCTTAGG AGGCTACATG GTTCATGAAA GTGGTGCAGC      2880

ACAGTTGTAG TTGTTACATA TAACACTATG TGCATTGTTT ATTTATATTT ACTTATTATA      2940

TATTTTTATA TAATTATATT TATATGAATA AATAAAACCA TAAATGAATA TATGCATGTA      3000

TATATACACA ACACAAATAA AGCTATCTGT TCATCTTTCC TCTATCTGAT GATGCAACAG      3060

GCTTACCATA TAAGAAATGC CATGAAATCA CAGGACACGC TACAGAAAGG AGGGTATAAA      3120

ATATAACTAT AACTATATTA ACTACTAATA CCAGCAGTAA CTGGAGGAAT ATTCCTTGCC      3180

TGGAAAAGCA ATTTCAATTA ACAGAATTAT TTTGTTGACA ACAAGTTTTT TATTTAACTT      3240

GTTAAGATCA TGTAGGGCAG GATTGGGAGA GGCAAAAAAA AAAAGCTTTA GAATAAGAA       3300

AAAATATAAT GCAGTTTAAT TGTTAAAACT ATATGATTAC AAGTTATTTT CTTTTATACT      3360

TGTATTTTTC TACATGTTCC AAATTTCCTA TATTGAACAT AAGAAGATCA AAATAAATAT      3420

CAAATCTACC TTATTAAATA GGCACCGATG GTTATATGTT AGTCTGCATC CAACAAAGGC      3480

AAAGCACACT TAAAAGGATG GTTGACTCTT TTGGAAAAGG CAAGTCATTT TTAGGAGATA      3540

CCACACATAA TAGAACACTT TAAACTTTGT ACTTATCTCA GTCTTGGCTA ATTCAGTAGA      3600

AAGTCAACAA ATGTCTGACA CTAGTTTTTA TATCTTCATA TTTCAGTTGC AGTTATTCTC      3660

TTTTTCTGTA TATATCTCTG AGATGCAAAT CTATATATGA TTATGTTAAT GAGCTTTTTT      3720

TTAATTCCTA ATAATACTTT GTTTTTGTAT GTCTTACTCC TAGGGGATT ATGGTGGCCC       3780

ACTTGTTTGT GAGCAACATA AAATGAGAAT GGTTCTTGGT GTCATTGTTC CTGGTCGTGG      3840

ATGTGCCATT CCAAATCGTC CTGGTATTTT TGTCCGAGTA GCATATTATG CAAAATGGAT      3900

ACACAAAATT ATTTTAACAT ATAAGGTACC ACAGTCATAG CTGAAGTAAG TGTGTCTGAA      3960

GCACCCACCA ATACAACTGT CTTTTACATG AAGATTTCAG AGAATGTGGA ATTTAAAATG      4020

TCACTTACAA CAATCCTAAG ACAACTACTG GAGAGTCATG TTTGTTGAAA TTCTCATTAA      4080

TGTTTATGGG TGTTTTCTGT TGTTTTGTTT GTCAGTGTTA TTTTGTCAAT GTTGAAGTGA      4140

ATTAAGGTAC ATGCAAGTGT AATAACATAT CTCCTGAAGA TACTTGAATG GATTAAAAAA      4200
```

```
ACACACAGGT ATATTTGCTG GATGATAAAG ATTTCATGGG AAAAAAAATC AATTAATCTG   4260

TCTAAGCTGC TTTCTGATGT TGGTTTCTTA ATAATGAGTA AACCACAAAT TAAATGTTAT   4320

TTTAACCTCA CCAAAACAAT TTATACCTTG TGTCCCTAAA TTGTAGCCCT ATATTAAATT   4380

ATATTACATT TCATATGCTA TATGTTATAG TTCATTCATT TCTCTTCACC ATGTATCCTG   4440

CAATACTGGT ACACGAACAC ACTTTTTACA AAACCACATA CCCATGTACA CATGCCTAGG   4500

TACACATGTG CATGCACTAC AGTTTAAATT ATGGTGTACC TAATGTAACC CCTAAATATT   4560

TTAGAAGTAT GTACCTATAG TTTTACCTCA AAAAAACCAG AAATCTCTAA AGACCAGTAG   4620

AAATATTAAA AAATGATGCA AGATCAAAAT GATTAGCTAA TTCTCCATAC ATAATCTGCA   4680

GATGATCTTC TTTGGTTGGC ATTTCAGGTG TGGCCATCAC CCAGAGTTAA ATAACACCTA   4740

ATCTAGGTGT TTACATGTAT TCATTATCCT AGTTATTTCA TGTAGTTTCT AATTCTTAAA   4800

GGAAAGAGGG TAATAGTTCT ATTTGTGTAA TTTGTTTCCT CCAAACTTAA GGCCACTTAT   4860

TTACACAAGA TATTTGTAGA TCTATTTTCC TAAAGCATTT CTTAAGTGCT CAGATCAGTA   4920

TCTAATTGAA GAAGTTTAAA AGTGTTTTGG TCATTAAAAA TGTACTTAAA TAGGTTAAAT   4980

CTAAGCCTTG CTGCTGTGAT TGGCTTCTAG CTCACTGCCT TTAAATTTTA AAAAATTTAA   5040

GAGGAAAATT TCCAAGTCTC CAAAGTTTTA TAAATACCCT TCATCAAGTC ATGCATTAAA   5100

GTATATATTG GAGAAAAAAA TAAAAATACT TTTCTCAACC TGGAAGATTT TAGCCTAATA   5160

AAGCTTTTTT GAAGTAAAAG ACAACTTGTA AAAGGAAAGA AACTAGTTTG TCTCAACTCT   5220

GTATTCATTT ATTTTTTTTT TGAAGTAGAG TGGAATCTGT TGAATCAGAT ATTTTATCAA   5280

GATATGTTTA TTTTTTCTTA TTTCATTTTA CAAAGTTCAC TCCTAATGCC ATATGTAACA   5340

GACATTTAAA TTTTGTGTTC TGTATAACAG CCAAATTATC ATATTTATCA TTGTATTTGT   5400

CATGCTTAGC TAAAGATCAT GTATTTGTTG AGAAATAGAA TAACAAAAAG TAATAGCATA   5460

GGCTTTGAAT TTTTGCAGAA ATCTTCCTGT ACAAAACACC TTTAAAAATA ATTTTTTGAA   5520

TGGTGTGAAT CCAGTAGTCC CATTTCTCTG ACTTAGTTTT CTTGAGTGAT TTTTATCAAG   5580

GCCAAGTCCC CAAACAATTC CCTACCAGCT CTTTAGAGTA CTGTTCAATC TGGACTAAAA   5640

TGGTTTTAAG TTTATGGAGA GCTTAGTCCA CAGAATATAG GGCGGCGAGT CCAGAAATGC   5700

TTATACAATT TTTTTTTCAT AATAAGATAT GTGCTGGCAT CAAGAAACTT AAAGTGGAAG   5760

CAAAAAGACA TCCAACTAGT TGCTGGTCTC TATCATCTTA TCTGATGGTA TTTCTATTTT   5820

CCTTATATAA TACACCATTT TAGTAAGAAC TCCTAGAAAT TTCAAGAGCA TATTGCCAAA   5880

ATATAAAGTA TATTTCATAG TTTCTTCTGG CTGAACCAGT GAAATTTTAT TATTGCATAT   5940

TAATGATATT TGTAAAACTT TTATAAAAAT TGTCATAATT TTAAATACTC ACATTTTAAA   6000

AATACTTCTT TAATGACTCT TCCTCTAAAT TTCCTGGAAA TACAGATAAA GATTAGCTAG   6060

ATACAAGATA CAGCTAAGTA TTTAGACATT TTGAGGCTAG TATTTTTCAT TTTATTAAAG   6120

GCTAAAAACA ATACCACCAA TAAATCATCA AACAAACCGT ACAAAGTAAT TCTCTCTTTG   6180

GGAGGCTCCT TTCGTGATAG AGGGACATGG GTGGAATTGA CAATGAAACT TAGATGAACA   6240

AGGTCCATGT TATTTTAGGT GGTAGAACAG GGTAGAGTCA TGTCATTATT TGCTGGTGGA   6300

AGACACTATT TACCAGGTGT TCTTTGCTGA ATAAATCATT AAACATTTTT AAAAATCCAA   6360

CAATCCACTT TATTTTGTGT CATTGACAAA AGGATCTTTT AAATCAGAAG GTTTCAATGC   6420

AATTTTTGGT TTGGCTGTTT GAATAATGGT TATGTACTGT TATAATTGTA GACATTTTCT   6480

CACGTCTACC AGGAATTGAA GTGTAAAACT AAAATATTTT TCATAATGCC TCTGCCGTGC   6540

AGAAGGAATG ATAATCCTTT TGTATACTTC TTTAATTTTA TTGTAAAATG TGTAATGACT   6600
```

```
TTTACCTATA TGCTGTGGGC AGGTCCTCAG TAAAATCTAT TGAGTCAATT TCTAGTATTA    6660
ACAGGCTTTT GCTTGCTATC TAAGTGTTTC AAATTATGGG AAGTGTGAGA CACTGGAAGG    6720
CAAGAAAATT AACAATAATG GCATGTGATA GCAAAATTGT ATTTCACTTA TTCCTGTGAA    6780
TATTTCTTGT TGGTACCAAT GGTACTGTAC AAAGTGAATG TTATAGCCAC AACATTCTCT    6840
TGAAAAGAAC ACTGTCAAGA AGTGGGAAAT TGCTGTCAGG CATTTCATTG TTGTTTTTAA    6900
ACTTTTTTAA AAGAAATACT GGTTTTGCAA TATAGAGATC ATGTGGTAAA GAATTTTAAT    6960
AAGATCTTAT ACTAAAAAGC CTTAAATCAA TTTATTGAGA TTCAAAAAAT ACTATTATAA    7020
TTAATTACAT CCCATACATA TAGGCAAACT CATTTAAAAA ATAAAACTAA TTTTGGTAAA    7080
AGTACATGGC CTTTGTTTTT AAAATACATA ATTTTAAAAT AAATCACTTG TCATGATAAA    7140
GTCCAAAAAG AAGTTATCAT TCAACATTCA ACTAAGGTTG GAGCTAAGAA TTTACTAATA    7200
CAAAAAAAAG TTAAAATTTT TTGGACCATA TATATCTTGA CAGTGTAACT TTTAAGTAGG    7260
TTCATTTCCA TTTGCACAGA AAGTTTCTGT CTTTAGGAAA CTGAAAATGA AATACTGTGG    7320
ATGCATGACT GTTTGTCTTG TATGTAAATA GGAAAATAAT AAGCTGCCTA TTGAGTGGTA    7380
TAGCTGTATG CTTACCCAAA AAAGGGAACA CTGTGGTTAT GACTTGTATT ATAAACTTTC    7440
TGTAGTTAAT AAAGTTGTTA TTTTTATAAC CATGATTATA TTATTATTAT TAATAAAATA    7500
TTTTATCAAA ATGCTTATTT TCTCTGTTAT GTTATTTACA TGTACATATT TATATCTGTC    7560
TTAGGGCCTA AATGCAGAAA ATAGCAATGT TGACTTCACT GACAAAAATA AAATACACGT    7620
TTTTGCAAAA ACTATAATAC AACTTGTTAT AGAACTAAGA CAAAAATCAT TATTTTATTC    7680
CAACTAATAT CCACAGCAAT ATAGTTGGTC TTCAGTAAAC CATTAATCTC TATGCACTTT    7740
AGTTTCTCCC ACC                                                      7753
```

CHROMOSOME DNA CODING FOR HUMAN HEPATOCYTE GROWTH FACTOR

This is a continuation of copending application Ser. No. 07/705,741 filed on May 28, 1991.

FIELD OF THE INVENTION

The present invention relates to a chromosome DNA which codes for human hepatocyte growth factor, a recombinant expression vector capable of expressing said DNA, a transformant transformed with said expression vector and a method of cultivating said transformant and producing recombinant human hepatocyte growth factor from the culture.

The DNA and polypeptide of the present invention are expected to serve well for hepatocyte cultivation reagents, liver regeneration promoters, basic research on liver function, research on the action of various hormones and drugs on hepatocytes, research on the carcinogenesis mechanism of hepatoma, clinical diagnostic reagents using a DNA probe or antibody against said polypeptide and therapeutic drugs for liver diseases.

BACKGROUND OF THE INVENTION

Traditionally, epithelial cell growth factor (EGF), fibroblast growth factor (FGF), nerve cell growth factor (NGF), platelet-derived growth factor (PDGF), endothelial cell growth factor (ECGF) and other polypeptides have been known to possess cell growth activity. In addition to those cell growth factors, a polypeptide which shows hepatocyte growth activity in vitro was partially purified from serum of rats with regenerated liver by Nakamura et al. in 1984, and named hepatocyte growth factor (hereinafter abbreviated as HGF) [Biochem. Biophys. Res. Commun., 122, 1450 (1984)].

Until the discovery of HGF, it had been impossible to cultivate hepatocytes in vitro: they showed no growth even in the presence of mammalian serum which allows vigorous growth of various lines of established cells, and they usually fell down off from the wall of cultivation vessel in about 1 week. In the presence of HGF, hepatocytes showed very good growth, and their cultivation became possible [Biochem. Biophys. Res. Commun., 122, 1450 (1984)]. Other workers confirmed that this HGF activity was present also in blood after partial hepatectomy and in blood of fulminant hepatitis patients. Although methods of purification, chemical properties and biological properties of HGF were elucidated by many workers since then, the amino acid structure of HGF or a polypeptide possessing similar hepatocyte growth activity has not been identified.

With this background, the present inventors have made a series of investigations of HGF separated and purified from various tissues such as rat platelets, and found that this platelet-derived HGF comprises two kinds of subunits and it allows hepatocytes to grow very well in vitro, and succeeded in identifying 27 amino acid residues of a partial amino acid sequence of HGF (Japanese Patent Application No. 311866/1988). Furthermore, the inventors used an oligonucleotide probe synthesized on the basis of the identified amino acid sequence to select and identify the cDNA which codes for rat hepatocyte growth factor from a rat liver cDNA library, and succeeded in selecting and identifying the cDNA which codes for human hepatocyte growth factor from a human liver cDNA library using the obtained rat cDNA [Nature, 342, 440 (1989); Japanese Patent Application No. 142697/1989]. Also, the cDNA which codes for human hepatocyt growth factor was isolated from human placenta [Biochem. Biophys. Res. Commun., 163, 967–973 (1989)] and from human leukocytes [Biochem. Biophys. Res. Commun., 172, 321 (1990)] in the same manner.

Since HGF in vivo is a polypeptide secreted in only trace amounts from organs such as liver, brain, lung, bone marrow, spleen, placenta and kidney or from blood cells such as platelets and leukocytes, there are many problems such as starting material availability. HGF yield and stable supply. To utilize this HGF for hepatocyte cultivation or hepatocyte research, it is necessary to clarify its structure and massproduce HGF or a polypeptide possessing similar activity by gene recombination technology. Also, to clarify the relationship between diseases and HGF gene anomalies in the study of the function of HGF in vivo, it is desired to analyze the structure of the HGF gene on chromosome, which forms the basis thereof.

SUMMARY OF THE INVENTION

With the aim of solving the problems described above, the present inventors have made intensive investigations, and found that a chromosome DNA containing the base sequence which codes for human HGF polypeptide can be obtained from a chromosome DNA library prepared from human placenta chromosome DNA using a cDNA containing the base sequence which codes for human liver derived HGF as the probe. Furthermore, the inventors have obtained a transformant transformed with a recombinant expression vector containing said chromosome DNA, and found that the human HGF gene is expressed by cultivating said transformant, which resulted in completion of the present invention.

Accordingly, the present invention provides a chromosome DNA having the base sequence which codes for human hepatocyte growth factor, a recombinant expression vector capable of expressing said DNA, a transformant transformed with said expression vector and a production method for human hepatocyte growth factor characterized by cultivating said transformant and harvesting recombinant human hepatocyte growth factor from the culture.

DETAILED DESCRIPTION OF THE INVENTION

Figure 1:
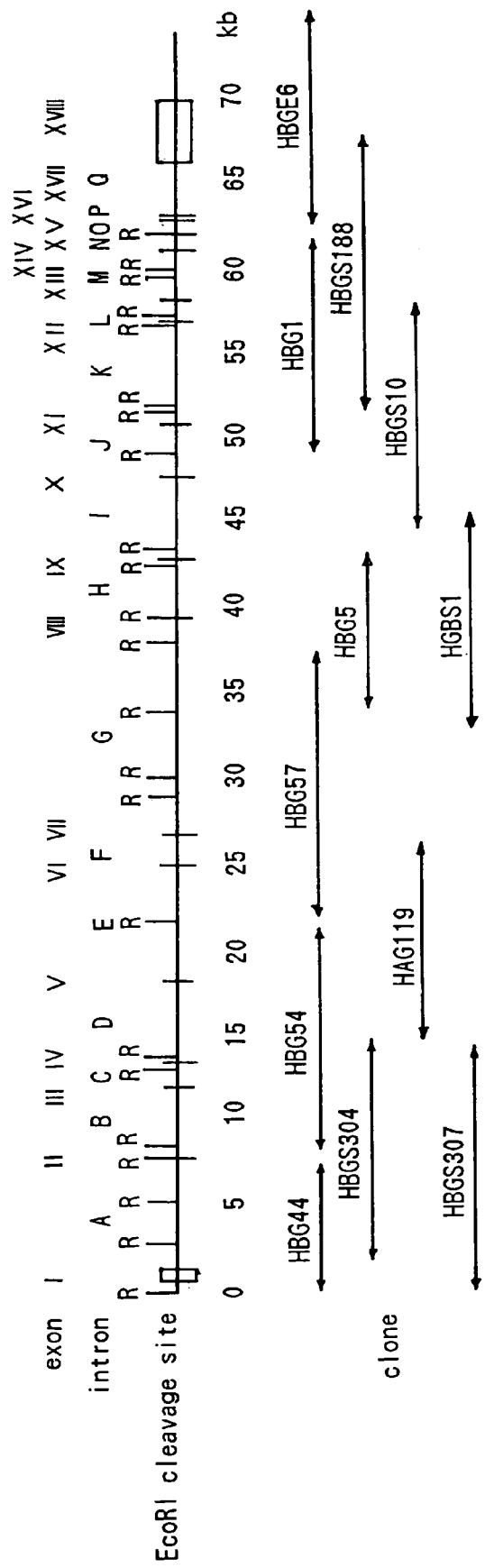
FIG. 1 is the restriction enzyme EcoRI cleavage map of the chromosome DNA which codes for human HGF, showing the positions of respective clones.

The chromosome DNA of the present invention, which contains the base sequence which codes for human hepatocyte growth factor, an expression vector therefor and a transformant transformed therewith are prepared, for example, as follows:

(1) Chromosome DNA is isolated from a tissue such as human placenta or human liver, and a chromosome DNA library is prepared in accordance with the conventional method. (2) Using the cDNA or chromosome DNA which codes for human HGF, the above-mentioned human chromosome DNA library is subjected to screening to isolate the chromosome DNA which codes for human HGF, and the desired chromosome DNA is extracted from the isolated clone. It is also possible to use as the probe an oligonucleotide synthesized on the basis of the DNA sequence clarified by the present invention or amino acid sequence of human or animal HGF or the human HGF chromosome DNA obtained by the present invention to carry out human chromosome DNA library screening and extract the desired chromosome DNA which codes for human HGF from the isolated clone. (3) This chromosome DNA fragment which codes for human HGF is cut out using restriction enzyme and inserted into an expression vector. (4) The obtained recombinant expression vector is used to transform a host cell to yield a transformant. (5) This transformant is cultivated, and human HGF can be harvested and produced from the resulting culture supernatant. It is also possible to obtain a DNA containing the base sequence which codes for the human HGF of the present invention from the recombinant expression vector in the transformant cell by restriction enzyme treatment.

The processes of the present invention are hereinafter described in detail.

(1) Isolation of chromosome DNA and preparation of chromosome DNA library

Chromosome DNA which codes for human HGF can be obtained from human organs such as liver, kidney, spleen, lung, brain, bone marrow and placenta, human blood cells such as leukocytes, megakaryocytes and lymphocytes and human derived established cells such as HeLa cells. For example, said DNA can be prepared by phenol extraction and dialysis of the chromosome DNA obtained from a surfactant treated suspension of human organ, blood cells or established cells by the method of T. Maniatis et al. described in Molecular Cloning, Cold Spring Harbor Laboratory, 1982, p. 269.

Also, various chromosome DNAs derived from animal tissues such as human placenta chromosome are commercially available from Clontech and other firms.

By partially or completely digesting these chromosomes DNAs using restriction enzyme in accordance with, for example, the method of T. Maniatis et al. (Molecular Cloning, Cold Spring Harbor Laboratory, 1982, p. 269) and inserting them into cosmid or phage vector, a chromosome DNA library can be prepared. Examples of the cosmid vector to insert the chromosome DNA therein include pWE15 (Stratagene), which is replicable in *Escherichia coli* and animal cells. Examples of the phage vector to insert the chromosome DNA therein include EMBl3 (Stratagene) and λ gtWES (Bethesda Research Laboratories, Inc.). These vectors are not limited to the examples given here as long as they are those retained, replicated and amplified in the host cell.

Examples of the method of inserting chromosome DNA into cosmid or phage vector to yield a chromosome DNA library include the method of T. Maniatis et al. (Molecular Cloning, Cold Spring Harbor Laboratory, 1982, pp. 269 and 295). Also, like chromosome DNAs, various chromosome DNA libraries are commercially available from Clontech and other firms.

(2) Cloning of chromosome DNA library

The recombinant cosmid, phage or other vector obtained as a chromosome DNA library is harbored in an appropriate host cell such as *Escherichia coli*. Examples of *Escherichia coli* strains which can serve as the host include AGI and LE392 (Stratagene). The chromosome DNA library prepared using the cosmid or phage vector can be harbored in a previously grown host cell by the in vitro packaging method or another method (Molecular Cloning, Cold Spring Harbor Laboratory, 1982, p. 249). From the transformant thus obtained, chromosome DNA can be finished by the plaque hybridization method [Science, 196, 180 (1977)] or another method using as the probe a $^{32}$P labeled DNA which codes for HGF of an animal such as rats or human HGF. The transformant thus cloned has chromosome DNA containing the base sequence which codes for the entire or partial amino acid sequence of human HGF.

Next, the recombinant DNA such as phage DNA is isolated from said transformant in accordance with the standard method (Molecular Cloning, Cold Spring Harbor Laboratory, 1982, p. 76) and digested with restriction enzyme, whereafter the base sequence of the chromosome DNA is determined. The base sequence of the obtained human HGF chromosome DNA is determined by, for example, the Maxam Gilbert chemical method [Proc. Natl. Acad. Sci. USA 74, 560 (1977)] or the Sanger dideoxy method [Proc. Natl. Acad. Sci. USA, 74, 5463 (1977)]. If necessary, it is possible to clone a cosmid, phage or other recombinant DNA containing a second chromosome DNA which can be ligated to the first chromosome DNA obtained in advance from the chromosome DNA library in the same manner as above using the obtained entire or partial chromosome DNA as the probe. This cloning process is repeated in a number of cycles where necessary.

(3) Construction of human HGF expression vector

A recombinant expression vector can be prepared by cutting out chromosome DNA using restriction enzyme from a cosmid, phage or other recombinant vector containing the cloned chromosome DNA which codes for the entire or partial amino acid sequence of human HGF and re-ligating it to the downstream of a vector promoter suitable for human HGF expression using restriction enzyme and DNA ligase.

More specifically, for increased expression efficiency of the human HGF of the present invention, the recombinant expression vector is constructed so that 1) a promoter, 2) a ribosome binding site, 3) an initiation codon, 4) a DNA containing the base sequence which codes for the human HGF of the present invention, 5) a termination codon and 6) a terminator are present therein in this order in the downstream direction of transcription.

Any DNA vector can be used for the present invention as long as it is replicable and amplifiable in the host. Examples of such DNA vectors include the yeast derived plasmid pRB15 (ATCC37062), virus SV40 (BRL Inc.), BPV (ATCC VR-703) and retrovirus gene derived vector. Particularly, for convenient expression of the human HGF of the present invention, it is preferable to use a vector derived from the gene of a virus such as SV40. For example, the recombinant expression vector wherein the above-mentioned cloned DNA which codes for human HGF is ligated to the later region of SV40 vector can be expressed by incorporating it into a simian cell line known as COS cells [Cell, 23, 175 (1981)].

As for promoters and terminators, there is no limitation as long as they suit to the host used to express the desired base sequence which codes for human HGF. Examples of promoters include GAP promoter and PGK promoter for yeast hosts, virus derived SV40 promoter, HSV1 TK promoter, metallothione in promoter and heat shock promoter for animal cell hosts such as mouse fibroblasts and Chinese hamster ovarian cells. Examples of terminators include CYC1 terminator for yeast hosts and SV40 terminator and HSV1 TK terminator for animal cell hosts. These promoters and terminators are used in appropriate combination according to the host used.

The DNA containing the base sequence which codes for the human HGF of the present invention is not subject to limitation as long as the polypeptide at which said DNA is expressed possesses hepatocyte growth activity. Examples of the DNA include the base sequences listed under SEQ ID NO:3–17 in the Sequence Table. Moreover, the DNA may have a base sequence resulting from partial substitution, deletion, insertion or combination thereof in the base sequence mentioned above. The DNA containing the base sequence which codes for the human HGF of the present invention may contain a translation initiation codon ATG and a translation termination codon TAA, TGA or TAG. Also, if necessary, more than one initiation codon or termination codon may be used in combination, or may be combined with another codon, and these combinations are subject to no limitation. Moreover, it is preferable that one or more kinds of genes capable of serving as a selection marker for the host transformed with this recombinant expression vector, such as the neomycin resistance gene and the DHFR gene, be contained in the vector at an appropriate position.

(4) Host cell transformation and cultivation

The human HGF recombinant expression vector thus constructed is introduced into the host by the protoplast method [Proc. Natl. Acad. Sci. USA, 75, 1929 (1978)], the calcium phosphate method [Science, 221, 551 (1983)], the DEAE dextran method [Science, 215, 166 (1982)], the electric pulse method [Proc. Natl. Acad. Sci. USA, 81, 7161 (1984)], the virus vector method [Cell, 37, 1053 (1984)], the microinjection method [Exp. Cell. Res., 153, 347 (1984)] or another method to prepare a transformant, wherein a yeast, animal cell and other host is such as mouse fibroblast C127 [J. Virol., 26, 291 (1978)] or Chinese hamster ovarian cell CHO [Proc. Natl. Acad. Sci. USA, 77, 4216 (1980)].

The obtained transformant is cultivated in a culture medium suitable to the host to produce the desired recombinant human HGF. The medium is supplemented with carbon sources, nitrogen sources, minerals, vitamins, serum, chemicals and other additives necessary for the growth of the transformant. Examples of media include YEPD medium (Genetic Engineering, vol. 1, Plenum Press, New York, 1979, p. 117) for yeast hosts and MEM medium containing not more than 20% bovine fetal serum, DMEM medium and RPM1640 medium (Nissui Seiyaku) for animal cell hosts. Transformant cultivation is carried out normally at a temperature of 20 to 45° C. and a pH of 5 to 8, with aeration and/or stirring added as necessary. When the host is an adhesive animal cell or the like, glass beads, collagen beads, acetylcellulose hollow fiber or another carrier is used. Medium compositions or cultivation conditions other than those described above may be used as long as they allow the transformant to grow.

(5) Purification of human HGF

The recombinant human HGF thus produced in the transformant or in the culture supernatant thereof may be separated and purified by a combination of known techniques such as salting out, solvent precipitation, dialysis, ultrafiltration, gel electrophoresis, gel filtration chromatography, ion exchange chromatography, reverse phase chromatography and affinity chromatography. Particularly preferred efficient methods are the combination of ammonium sulfate salting-out, S-Sepharose ion chromatography, heparin Sepharose affinity chromatography and phenyl Sepharose reverse phase chromatography and the combination of ammonium sulfate salting unit. S Sepharose ion chromatography and anti HGF antibody Sepharose affinity chromatography.

The recombinant human HGF thus obtained showed noticeable promoting activity on the growth of rat hepatocytes like rat liver-derived HGF and rat platelet-derived HGF.

Determination of HGF activity

HGF activity was determined in accordance with the method described in Proc. Natl. Acad. Sci. USA, 80, 7229 (1983) as follows: Hepatocytes were separated and purified from Wistar rats by the collagenase reflux method. The obtained rat hepatocytes were suspended in William E medium (Flow Laboratory) supplemented with 5% bovine serum, $2 \times 10^9$ M insulin and $2 \times 10^9$ M dexamethasone and sown over 24 well multiplates at a density of $1.25 \times 10^5$ cells/well. After cultivation in the presence of 5% $CO_2$, 30% $O_2$ and 65% $N_2$ at 37° C. for 20 hours, the medium was exchanged with William E medium supplemented with 0.1 μg/ml aprotinin, with simultaneous addition of a given amount of the subject sample. Fifteen hours later, 15 μCi/ml $^{125}I$ deoxyuridine was added at 10 μl/well. For the control group, 5 μg/ml aphidicolin was added 15 minutes before addition of $^{125}I$ deoxyuridine. Cultivation was continued for 6 more hours for $^{125}I$ labeling. After washing with two portions of PBS, pH 7.4, the cells were fixed in a cold 10% aqueous solution of trichloroacetic acid (TCA). The cells were solubilized with a 0.5 ml/well 1 N aqueous solution of sodium hydroxide, and their radioactivity was determined using a gamma counter. Also, a portion of the radioactivity-determined sample was taken and subjected to protein content determination by the Lorry method [J. Biol. Chem., 193, 265 (1951)]. The amount of $^{125}I$ uptake into hepatocytes upon addition of the subject sample was calculated as the count difference from the control, and the obtained value was converted to per mg rat hepatocyte protein to obtain the DNA synthesis activity (dpm/mg protein). The HGF activity of the subject sample corresponding to 50% of the DNA synthesis activity of hepatocytes obtained with 10 ng/ml epithelial cell growth factor in the same test was defined as 1 unit.

Determination of HGF content

HGF content was determined by the ELISA method as follows:

A solution of 25 μg/ml antihuman HGF antibody in 0.05 M sodium hydrogen carbonate was added to 96-well multiplates at 50 μl/well and incubated at 37° C. overnight. A PBS buffer containing 3% bovine serum albumin was added at 100 μl/well. After incubation at 37° C. for 30 minutes, the multiplates were washed with a washing solution prepared by adding 0.0025% Tween 20 to PBS buffer. The subject sample and standard sample, diluted with a diluent prepared by adding 0.5% bovine serum albumin and 0.05% Tween 20 to PBS buffer, were added at 100 μl/well. After incubation at 37° C. for 2 hours, the multiplates were washed with the washing solution. Biotin labeled antihuman HGF antibody diluted with the diluent to an appropriate degree was added at 100 ml/well. After incubation at 37° C. for 90 minutes, the multiplates were washed with the washing solution. Peroxidase-labeled streptoavidin (Amersham Corporation) diluted with the diluent to an appropriate degree was added at 100 μl/well. After incubation at 37° C. for 1 hour, the multiplates were washed with the washing solution. A 3 mg/ml o-phenylenediamine dihydrochloride solution was added at 100 μl/well, after the multiplates were kept standing at room temperature for 20 minutes, a 2N sulfuric acid solution was added at 100 µl/well, and the absorption at 490 nm was determined using a plate reader. A standard curve was drawn on the basis of the absorption values obtained in the presence of the standard sample, and the HGF content in the subject sample was calculated.

The present invention provides a bioactive peptide which allows hepatocytes to grow in vitro. When using the chromosome DNA of the present invention for production of human HGF with an animal cell host, the expression amount in expected to increase by the action of a transcription potentiating sequence which is presumably present in intron in comparison with the case using cDNA. This is particularly effective in the preparation of transgenic animals used as pathologic model animals. The recombinant human HGF of the present invention is useful as a clinical diagnostic reagent or therapeutic drug for liver diseases. In addition, the hepatocytes, grown and preserved by the action of the recombinant human HGF of the present invention are very useful for various purposes such as basic research on liver function, research on the action of various hormones and drugs on hepatocytes, research on the carcinogenesis of hepatoma, and as host cells for in vitro cultivation of hepatitis virus. Furthermore, the chromosome DNA of the present invention which codes for human HGF is useful as a DNA probe diagnostic reagent and for research on the function of HGF in vivo.

The present invention is hereinafter described in more detail by means of the following examples, but the invention is not to be interpreted as limited by these examples.

EXAMPLE 1

(1) Isolation of human chromosome DNA

Human chromosome DNA was extracted and purified in accordance with the standard method (Molecular Cloning, Cold Spring Harbor Laboratory, 1982, p. 269) as follows: After 5 g of human placenta frozen with liquid nitrogen was milled using a Waring blender, a solution comprising 50 ml of 0.5 M EDTA (pH 8.0), 100 µg/ml proteinase K and 0.5% sodium lauryl sarcosine was added, followed by treatment at 50° C. for 3 hours. The resulting solution was extracted with phenol several times, and the DNA-containing aqueous phase was dialyzed against a solution comprising 50 mM Tris-HCl buffer (pH 8.0), 10 mM EDTA and 10 mM NaCl overnight. To the internal solution, 100 µg/ml RNase was added, followed by treatment at 37° C. for 3 hours. After extraction with a phenol/chloroform mixture, the extract was dialyzed against a 10 mM Tris-HCl buffer (pH 7.5) containing 1 mM EDTA (hereinafter referred to as TE buffer) at 4° C. overnight. The resulting chromosome DNA (500 µg) was partially digested with the restriction enzyme EcoRI or MboI, extracted with a phenol chloroform mixture, precipitated with ethanol and then dissolved in 500 µl of TE buffer. The resulting solution was layered onto 38 ml of a linear sucrose solution (10% to 40%) comprising 1 M NaCl, 20 mM Tris-HCl buffer (pH 8.0), 5 mM EDTA and subjected to sucrose density gradient centrifugation at 26000 rpm, 20° C. for 24 hours using the L8 55 model Beckman ultracentrifuge equipped with an SW28 rotor. After centrifugation, the solution was fractionated into 0.5 ml portions, and a fraction containing 15 to 20 kb DNA was detected by agarose electrophoresis and collected. After dialysis against TE buffer at 4° C. overnight, the obtained fraction was precipitated with ethanol and dissolved in 1 ml of TE buffer.

(2) Preparation of vector DNA

Phage vector arms were prepared in accordance with the method of Maniatis et al. [Cell, 15, 687 (1978)] as follows: Charon 4A phage DNA (50 µg) completely digested with the restriction enzyme EcoRI [Science, 196, 161 (1977)] was treated in a TE buffer containing 10 mM $MgCl_2$ at 42° C. for 1 hour and then subjected to sucrose density gradient centrifugation in the same manner as (1) above, and the fraction containing both the left and right arms was dissolved in 100 µl of TE buffer. EMBL3 and EMBL4 phage vectors were purchased from Stratagene.

(3) Preparation of chromosome DNA libraries

The chromosome DNA obtained in (1) above (3 µg) and 1 µg of the phage vector DNA obtained in (2) above were ligated to each other using T4 DNA ligase, and the solution was subjected to in vitro packaging reaction using the in vitro packaging kit Giga Pack Gold (Stratagene). To the chromosome DNA digested with the restriction enzyme EcoRI was ligated with the Charon 4A or EMBL4 vectors, while the chromosome DNA digested with the restriction enzyme MboI was ligated with the EMBL3 vectors. The resulting ligated products were named HBG, HBGE and EBGS libraries, respectively. The human placenta chromosome DNA library commercially available from Clontech was named HAG library and also used in the following procedures.

(4) Preparation of DNA probes

The plasmid pBS subcloned from the HGF-encoding cDNA isolated from human liver (hHGF11) (FERM P 11050 deposited at the Fermentation Research Institute, Agency of Industrial Science and Technology, Ministry of International Trade and Industry, Japan) was digested with the restriction enzymes BamHI, EcoRI and PstI, and each resulting cDNA fragment was separated and purified by agarose electrophoresis The BamHi EcoRI 147 bp fragment is expected to hybridize with the chromosome DNA fragment which codes for Amino Acid Nos. 1–41 in Sequence Table; the EcoRI 847 bp fragment is expected to hybridize with the chromosome DNA fragment which codes for Amino Acid Nos. 42 323; the EcoRI EcoRI 678 bp fragment is expected to hybridize with the chromosome DNA fragment which codes for Amino Acid Nos. 324–549; the EcoRI-PstI 1271 bp fragment is expected to hybridize with the chromosome DNA fragment which codes for Amino Acid Nos. 550 728. The resulting DNA fragments were labeled with $[\alpha^{32}P]dCTP$ (Amersham) using the Multiprime DNA labeling system (Amersham) to yield DNA probes.

(5) Isolation of chromosome DNA which codes for human HGF and determination of its base sequence After each library obtained in (3) above was tritrated on *Escherichia coli* LE392 strain (Stratagene), about $4 \times 10^5$ recombinant phages were made to infect about $8 \times 10^9$ cells of *Escherichia coli* LE 392 strain at 37° C. for 15 minutes. Then, the cells were added to 40 ml of an LB medium containing 0.7% agar, heated at about 50° C., and the mixture was spread over four plates of 250 ml of an LB medium containing 1.2% agar, pre-solidified in petri dishes of 22 cm×22 cm in size. After plaque formation by cultivation at 37° C. for 12 hours, each plate was incubated at 4° C. for 1 hour and then kept in close contact with a nylon filter Hibond N (Amersham) for 30 seconds.

This nylon filter was immersed in a denaturant solution comprising 1.5 M NaCl and 0.1 M NaOH for 5 minutes and then immersed in a neutralizing solution comprising 1.5 M NaCl and 0.5 M Tris-HCl buffer (pH 7.2) for 15 minutes. After washing in 2×SSC buffer, the nylon filter was dried in air and treated at 80° C. for 2 hours to immobilize the DNA of each plaque onto the nylon filter. The obtained nylon filter was immersed and treated in a hybridization solution comprising 6×SSC buffer, 5×Denhardt's solution, 0.5% SDS and 20 μg/ml thermally denatured *Escherichia coli* chromosome DNA at 65° C. for 1 hour. The probe DNA of (4) above thermally treated at 100° C. for 5 minutes was added to the hybridization solution, and hybridization reaction was carried out at 65° C. for 16 hours. After completion of the reaction, the nylon filter was washed with three portions of 2·SSC buffer containing 0.1% SDS at 65° C. and then dried in air. This nylon filter was brought into close contact with the sensitization screen Lightning Plus (Du Pont) and the X ray film RX (Fuji Photo Film) and exposed in dark at 80° C. for 50 hours. All libraries were subjected to the same procedure: a total of about 200 positive clones were obtained from about 2×10$^6$ recombinant plaques. After each clone was subjected to secondary screening, phage DNA was isolated and purified. After restriction enzyme analysis, the obtained DNA was subjected to Southern blot analysis using human liver derived cDNA or separately obtained chromosome DNA, and the relative position of each clone and the position of exon containing were determined. Also, the base sequence of the exon containing DNA fragment was determined by the dideoxy method using Sequenase (United States Biochemicals) or Tth polymerase (Toyobo Co., Ltd.). With respect to the clone which was found to be a desired clone by base sequence analysis, the chromosome DNA insert was separated and purified by restrictive enzyme treatment and agarose electrophoresis, and used to prepare a DNA probe in the same manner as with the cDNA fragment. FIG. 1 is the restriction enzyme EcoRI cleavage map of the chromosome DNA which codes for human HGF, showing the positions of the exons and the positions of the twelve obtained representative clones HBG44, HBG54, HBG57, HBG1, HBGE6, GBGS304, HBG5, HBGS188, HAG119, HBGS10, HBGS307 and HBGS1. For the analysis, phage DNAs subcloned to plasmid vector were mainly used, including pHBGS307 (FERM P-11819), pHAG119 (FERM P-11811), pGBGS1 (FERM P 11816), pHBGS10 (FERM P 11817), and pHGBS188 (FERM P 11818), prepared by inserting the respective inserts HBGS307, HAG119, HBGS1, HBGS10 and HBGS188 into the SalI site of bluescript SKM13 (Stratagene), and pHBG5705 (FERM P 11813), pHBG5712 (FERM P-11814), pHGB5701 (FERM P 11812) and pHBE6 (FERM P 11815), prepared by inserting the first, second or third EcoRI insert from the 5' side of HBG57 or the entire insert of HBGE6, respectively, into the EcoRI site of bluescript SKM13+.

SEQ ID NO:3–17 in Sequence Table are the base sequences of respective exons and vicinities thereof. When comparing the base sequence of the leukocyte derived cDNA which codes of human HGF and that of the obtained chromosome DNA, it is speculated that the amino acid sequence of human HGF is encoded in the range of about 70 kb by 18 exons divided by 17 introns. The amino acid sequences encoded by respective exons are given in Table 1. The two kinds of cDNA which were isolated from human leukocytes, and coded for the amino acid sequences of SEQ ID NO: 1–2 (Japanese Patent Application No. 152474/1990) are estimated as resulting from the process of splicing because the difference therebetween is located at the 5' end of exon V (see SEQ ID NO: 7). The 5' nontranslation region and 3' nontranslation region are estimated as encoded respectively by exon 1 which codes for the initiation codon ATG, and exon XVIII which codes for the termination codon TAG, adjacent to the amino acid code region.

TABLE 1

| Exon No. | Encoding Sequence Table Amino Acid No. of Amino Acid Sequence, SEQ ID No 1 | Encoding Sequence Table Amino Acid No. of Amino Acid Sequence, Sequence No. 2 |
|---|---|---|
| I | 1–30 | 1–30 |
| II | 30–85 | 30–85 |
| III | 85–123 | 85–123 |
| IV | 123–161 | 123–161 |
| V | 161–209 | 161–204 |
| VI | 209–249 | 204–244 |
| VII | 249–289 | 244–284 |
| VIII | 289–347 | 284–342 |
| IX | 347–390 | 342–385 |
| X | 390–424 | 385–419 |
| XI | 424–469 | 419–464 |
| XII | 469–482 | 464–477 |
| XIII | 482–514 | 477–509 |
| XIV | 514–539 | 509–534 |
| XV | 539–586 | 534–581 |
| XVI | 586–622 | 581–617 |
| XVII | 622–670 | 617–665 |
| XVIII | 671–728 | 666–723 |

(6) Construction of human HGF expression vector for simian COS cells

Figure 2:
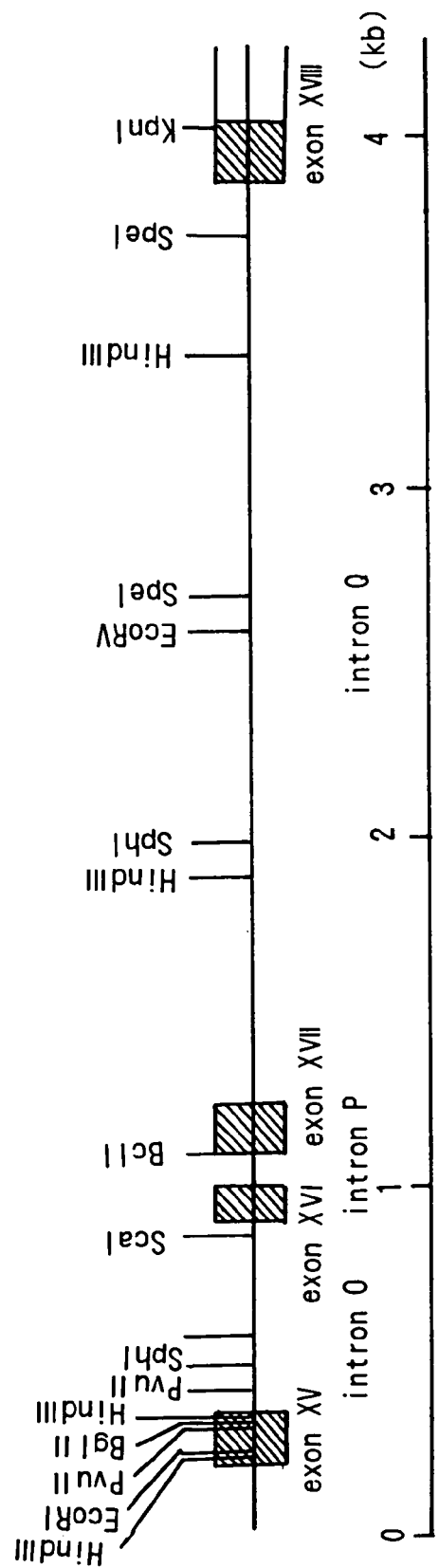
FIG. 2 is the restriction enzyme map around exons XV through XVIII of the chromosome DNA.
Figure 3:
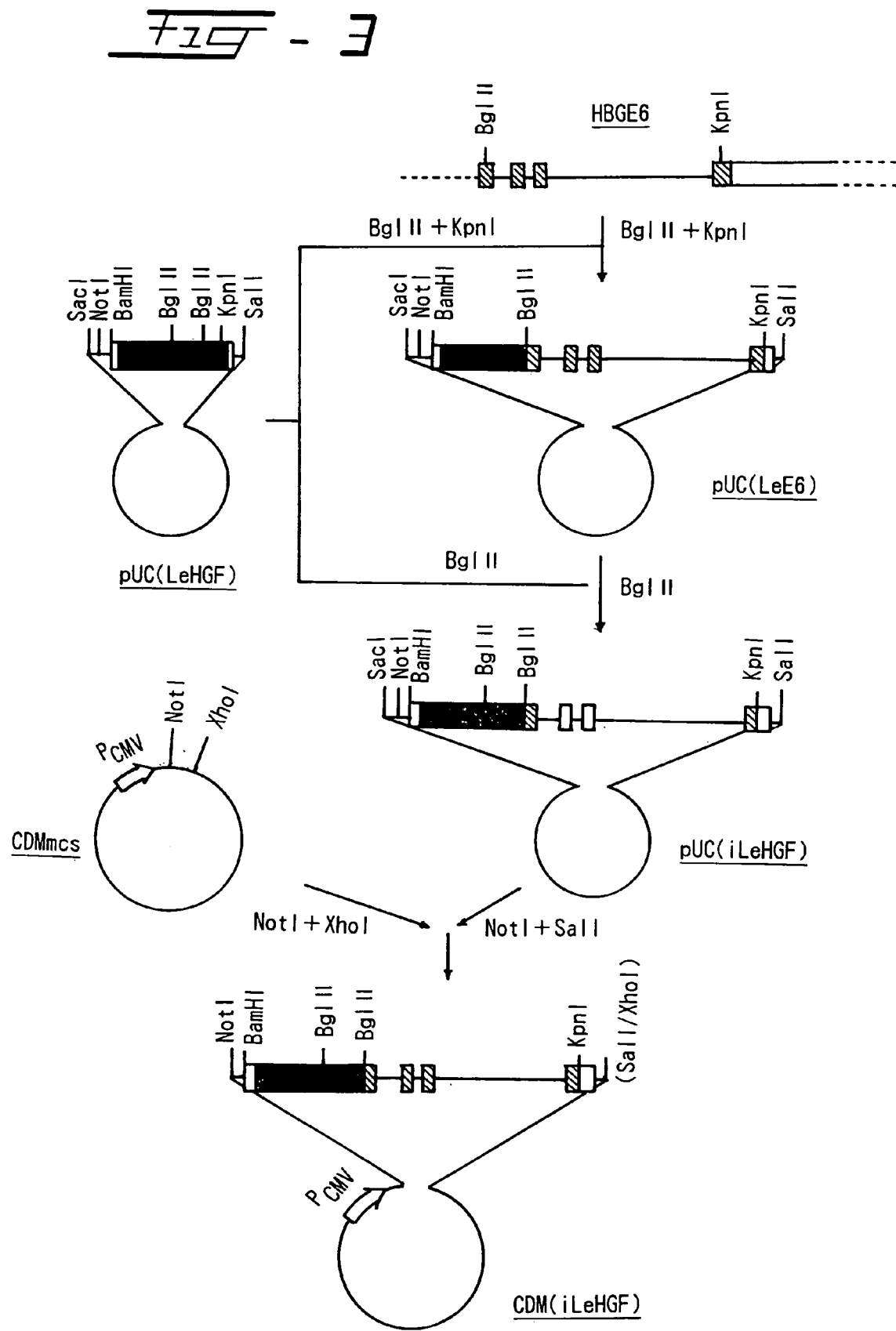
FIG. 3 is the construction scheme for the human HGF expression vector for simian COS cells.

The chromosome DNA which codes for human HGF is about 70 kb in length and is considered to be unsuitable for the construction of expression vector. For this reason, a region having an available restriction enzyme cleavage site in the exon was selected, and a hybrid gene was prepared by replacing a part of cDNA with the chromosome DNA. As shown in FIG. 2, there is neither restriction enzyme BglII cleavage site nor restriction enzyme KpnI cleavage site between the BglII cleavage site in exon XV and the KpnI cleavage site in exon XVIII on the chromosome DNA; therefore, use of this region for expression vector construction was considered as appropriate. The construction scheme for the human HGF expression vector CDM(iLeHGF) for simian COS cells is given i FIG. 3. HBGE6 phage DNA, one of the chromosome DNA clones obtained in (5) above from an HBGE library, was digested with the restriction enzymes BglII and KpnI and subjected to agarose electrophoresis to separate and purify a 3.8 kb DNA fragment which codes for Amino Acid Nos. 579–725 of SEQ ID NO: 1. pBS (LeHGF) (Japanese Patent Application No. 152474/1990) obtained by subcloning the leukocyte derived cDNA which codes for human HGF to bluescript KSM13− (Stratagene) via adapter was digested with the restriction enzymes SacI and SalI to yield a 2.2 kb DNA fragment, which was inserted into pUC18 (Toyobo Co., Ltd.) previously digested with the same restriction enzymes as above to yield pUC(LeHGF). After digestion with the restriction enzymes BglII and KpnI, this pUC(LeHGF) was subjected to agarose electrophoresis to separate and purify a 4.0 kb DNA fragment which codes for Amino Acid Nos. 1–407 of SEQ ID NO: 1. The two kinds of DNA fragments thus obtained (the 3.8 kb DNA fragment and the 4.0 kb DNA fragment) were ligated to each other using T4 DNA ligase to yield pBC(LeF6), which was digested with the restriction enzyme BglII and then treated with alkaline phosphatase. Thereto was ligated the 512 bp DNA fragment which codes for Amino acid Nos. 408–578 of SEQ ID NO: 1, obtained by separating and purifying the above mentioned pUC(LeHGF) using T4 DNA ligase after digestion with the restriction enzyme BglII, whereby pUC (iLeHGF) was obtained. The obtained pUC(iLeHGF) was digested with the restriction enzymes NotI and SalI. Then, the plasmid CDMmcs prepared by replacing the HindIII- XbaI restriction fragment of the expression vector CDM8 for COS cells (Invitrogen) with the HindIII-XbaI restriction fragment which codes for the multicloning site of the plasmid pRe/CMV (Invitrogen), was digested with the restriction enzymes NotI and XhoI and ligated with the above-mentioned digestion product using T4 DNA ligase to yield the expression vector CDM(iLeHGF) for human HGF.

(7) Transformation of simian COS cells and expression of human HGF gene

The CDM(iLeHGF) plasmid DNA obtained in (6) above was precipitated with ethanol and dissolved in 10 mM PBS buffer to a final concentration of 20 μg ml. Then, COS-1 cells (ATCC CRL-1650) in the logarithmic growth phase grown in DMEM medium (Nissui Seiyaku) containing 10% bovine fetal serum (Gibco) were washed with two portions of 10 mM PBS buffer, trypsinized, further washed with three portions of the same buffer and suspended in the same buffer to a final cell concentration of $2 \times 10^7$ cells/ml. The resulting plasmid DNA solution (250 μl) and cell suspension (250 μl) were mixed, and this mixture was kept standing with ice cooling for 10 minutes. To this iced plasmid/cell mixture a high voltage pulse was supplied using the high voltage pulsate gate introducer ZA 1200 (PDS) under conditions of an applied voltage of 4 kV/cm and a pulse time of 20 milliseconds. The obtained cells were diluted with the medium described above and cultivated in the presence of 5% $CO_2$ at 37° C. for 3 days. At day 3 of cultivation, the HGF activity in the culture supernatant was determined to be 15 U/ml using the above-mentioned rat hepatocytes. Also, the HGF content in the culture supernatant was determined to be 50 ng/ml by the above-mentioned ELISA method. On the other hand, CDM8, an expression vector not incorporating the HGF gene, was introduced into COS-1 cells in the same manner, and the cells were cultivated, but the culture supernatant was found to contain no HGF.

---

What is claimed is:

1. An isolated DNA molecule having the nucleic acid sequence of SEQ ID NO: 17.

2. A recombinant expression vector comprising residues 579–7725 of SEQ ID NO: 17.

3. The recombinant expression vector as claimed in claim 2, wherein the vector is derived from a yeast-derived plasmid, virus SV40, BPV or a retrovirus.

4. A transformant with the vector of claim 2.

5. The transformant of claim 4, which is obtained by transforming a host selected from the group consisting of yeasts and animal cells.

6. The transformant of claim 5, wherein the animal cells are mammalian cells.

7. The transformant of claim 5, wherein the animal cells are simian COS cells.

8. A method of producing a recombinant human hepatocyte growth factor, which comprises cultivating the transformant of claim 4 and harvesting the recombinant human hepatocyte growth factor from the culture.

* * * * *